United States Patent
DeFranks et al.

(10) Patent No.: US 11,266,352 B2
(45) Date of Patent: Mar. 8, 2022

(54) MONITORING METHODS AND CUSHIONING STRUCTURES

(71) Applicant: Dreamwell, Ltd., Doraville, GA (US)

(72) Inventors: Michael S. DeFranks, Atlanta, GA (US); Mackenzie Prestera, Atlanta, GA (US); John-David Velilla, Alpharetta, GA (US); Brian Anderson, Atlanta, GA (US); Kevin Chirackal, Lawrenceville, GA (US); Martin Ramsden, Lawrenceville, GA (US); Taneka Fields, Lilburn, GA (US)

(73) Assignee: DREAMWELL, LTD., Doraville, GA (US)

(*) Notice: Subject to any disclaimer, the term of this patent is extended or adjusted under 35 U.S.C. 154(b) by 365 days.

(21) Appl. No.: 16/420,586

(22) Filed: May 23, 2019

(65) Prior Publication Data

US 2019/0365328 A1 Dec. 5, 2019

Related U.S. Application Data

(60) Provisional application No. 62/677,909, filed on May 30, 2018.

(51) Int. Cl.
*A61B 5/145* (2006.01)
*A61B 5/00* (2006.01)
*A61B 5/1477* (2006.01)

(52) U.S. Cl.
CPC .......... *A61B 5/6891* (2013.01); *A61B 5/0004* (2013.01); *A61B 5/1477* (2013.01); *A61B 5/14517* (2013.01); *A61B 5/4266* (2013.01)

(58) Field of Classification Search
CPC ......... A61B 5/00; A61B 5/145; A61B 5/1477; A61B 5/6892; A61B 5/14517;
(Continued)

(56) References Cited

U.S. PATENT DOCUMENTS

| 10,238,222 | B2 * | 3/2019 | Rao | A61F 7/0085 |
| 2010/0170042 | A1 * | 7/2010 | Rose | A47C 27/15 |
| | | | | 5/698 |
| 2016/0320332 | A1 | 11/2016 | Hsiung et al. | |

FOREIGN PATENT DOCUMENTS

| CN | 107811453 A | | 3/2018 |
| CN | 107860809 A | * | 3/2018 |
| WO | 2016174465 A1 | | 11/2016 |

OTHER PUBLICATIONS

E. Garcia-Cordero et al., "Embedded passive nano-liter micropump for sweat collection and analysis," 2018 IEEE Micro Electro Mechanical Systems (MEMS), 2018, pp. 1217-1220, doi: 10.1109/MEMSYS.2018.8346782. (Year: 2018).*

(Continued)

*Primary Examiner* — Eric J Messersmith
(74) *Attorney, Agent, or Firm* — Cantor Colburn LLP

(57) ABSTRACT

Mattress assemblies and pillows are provided that include a flexible biosensor array provided on a layer of the mattress assembly for sensing an electrical conductivity associated with sweat emitted from an end user of the mattress assembly and producing an ionic concentration of at least one electrolyte; and a processor connected to the flexible biosensor array for interpreting the ionic concentration of the at least one electrolyte. Also disclosed are processes for monitoring and analyzing sweat from an end user of the mattress assemblies and pillows.

18 Claims, 8 Drawing Sheets

(58) Field of Classification Search
CPC . A61B 5/6891; A61B 5/14539; A61B 5/0004; A61B 5/4266; A61B 2562/029; A61B 2562/046; G01N 27/414
See application file for complete search history.

(56) References Cited

OTHER PUBLICATIONS

International Preliminary Report on Patentability dated Dec. 10, 2020 for International Patent Application No. PCT/US2019/033682.
Search Report and Written Opinion dated Sep. 19, 2019 for International Patent Application No. PCT/US2019/033682.
Khanna, V.K., "Ion-Sensitive Field-Effect Transistor (ISFET)-Based Chemical Sensors", In: "Sensor Technology Series: Chemical Sensors Comprehensive Sensor Technologies: vol. 5 Electrochemical and Optical Sensors", Jul. 1, 2011, Momentum Press, XP055271257, pp. 171-274.
Communication of European Publication Number and Information on the Application of Article 67(3) EPC for Application No. 19737597.5 dated Mar. 17, 2021, 1 page.

* cited by examiner

_US 11,266,352 B2_

MONITORING METHODS AND CUSHIONING STRUCTURES

CROSS REFERENCE TO RELATED APPLICATIONS

This application is a non-provisional of and claims the benefit of U.S. Provisional patent application Ser. No. 62/677,909, filed May 30, 2018, which is fully incorporated herein by reference in its entirety.

BACKGROUND

The present disclosure generally relates monitoring methods and cushioning structures including pillows, mattress pads, and mattress assemblies. More particularly, the monitoring methods and structures include various biosensor arrays configured to monitor and analyzing sweat of an end user of the cushioning structure.

Sensing systems can be used with structures to provide nonintrusive, continuous health monitoring. Commercialization of physical sensors in mattresses has already been achieved, while chemical sensing within the same platform is still in its infancy.

As electronics continue to become smaller, the sensors market has penetrated deeper into our daily lives, ranging from personal use to industrial use, among other applications. Mainstream commercial sensors in the market today largely rely on physical sensors, such as accelerometers and gyroscopes within smartphones, to track movement. Wearable sensors of this type have also emerged, allowing for more continuous and less intrusive capture of data. Wearable chemical sensors, however, remain a very active subject of research, with recent work focused on sweat analysis to assess one's health. Compared to blood, sweat is a particularly attractive analyte since it can be acquired non-invasively and contains chemical markers with significant physiological correlation. Despite the many uses of wearable sensors, in particular when the user is in transit and activity tracking is of interest, there exist applications where wearing a device is not practical or even possible.

BRIEF SUMMARY

Disclosed herein are cushioning structures such as mattress assemblies and/or pillows including a biosensor array for monitoring and analyzing sweat emitted from an end user.

The disclosure may be understood more readily by reference to the following detailed description of the various features of the disclosure and the examples included therein.

BRIEF DESCRIPTION OF THE SEVERAL VIEWS OF THE DRAWINGS

Referring now to the figures wherein the like elements are numbered alike.

DETAILED DESCRIPTION

The present invention is generally directed to health monitoring while lying on a cushioning articles such as a mattress structure using in-built sensors, which for mattress applications can be used both for everyday sleep analysis, as well as in-patient monitoring for bed-bound patients. More particularly, the present invention is directed to development of flexible chemical sensor arrays embedded in the cushioning article, e.g., mattress assemblies and/or pillows for sweat-based health monitoring. Since humans spend an average of one third of their lives lying on mattresses, they represent a unique yet heretofore untapped opportunity to monitor one's health and enable smart home systems that tailor our environments to optimize our well-being. Unlike the wearable sensors noted above, in-built mattress sensors would not require user installation or training and would therefore facilitate use. They also do not interfere with one's comfort, or force a change of habit in terms of what is worn during sleep.

As will be described in greater detail below, the flexible chemical sensor arrays have been integrated into cushioning articles such as mattress materials to detect an electrical conductivity associated with sweat emitted from an end user of the mattress assembly corresponding to pH, which is tied to various analyte such as an electrolyte and lactic acid concentrations, among other constituents, i.e., the electrical conductivity provides information related to an ionic concentration of at least one electrolyte. The individual sensor can be flexible or rigid, e.g., multiple rigid sensors connected via flexible interconnects. Although reference will be made herein to mattress and pillow applications, other suitable cushioning articles include, without limitation, seat cushions, sofa cushions, dermal pads, or like applications, wherein sweat monitoring is desired.

A low temperature and scalable microfabrication process is also described, with prototypes demonstrated on both silicon and flexible polyimide substrates. The chemical sensors are integrated with three commonly used mattress fabrics to demonstrate suitable and effective liquid-absorbing interfaces for the sensor's surface. By leveraging an extended gate sensor configuration, results are presented herein on the performance of these sensors when integrated into the mattress material, the effect of decreasing deposition temperature for the pH-sensitive dielectric thin film, and the stability of the on-chip reference electrode.

Figure 1:
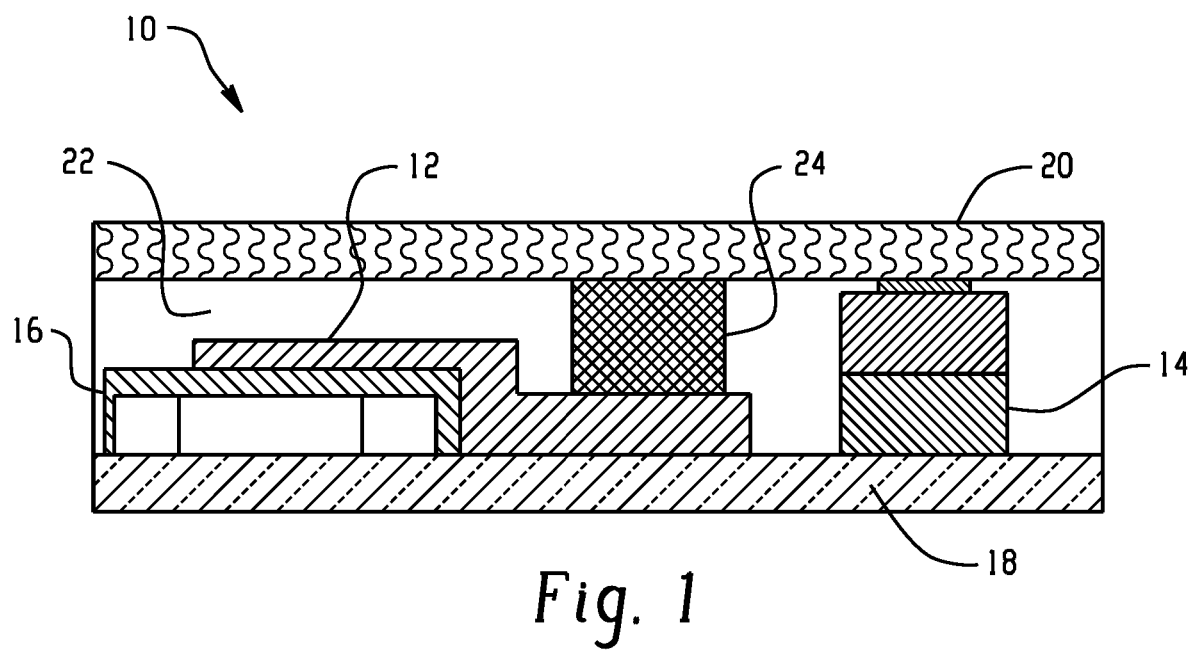
FIG. 1 ("FIG.") is a cross sectional view of a sensing unit for a biosensor array for use in a mattress assembly and/or pillow in accordance with one or more embodiments of the present disclosure.

FIG. 1 depicts a cross-section of a single sensing unit in accordance with one or more embodiments of the present invention. The single sensing unit single sensing unit 10 is shown in contact with a sweat absorbing fabric 2 generally includes a sensor electrode 12, a reference electrode 14, and a field effect transistor (FET) transducer 16. The entire platform is fabricated on an insulating substrate 18, which can include, for example, silicon dioxide, polyimide, a fabric or like insulating material. The sensor electrode 12 includes an alumina ($Al_2O_3$) thin film deposited on gold. $Al_2O_3$ can be used since it can be deposited with high quality at a wide range of temperatures and has been demonstrated to be pH sensitive. To enhance specificity, an analyte-specific layer can be added on top of the $Al_2O_3$, which will dictate that any change in potential observed at the surface of the $Al_2O_3$ is due to a change in concentration of a specific ion in question. In close proximity to the sensor electrode, a reference electrode 14 is formed. An exemplary reference electrode is of the Ag/AgCl type, which is well known in the art. The sensor electrode is connected to the gate electrode of a charge-sensitive field-effect transistor (FET) 16. The separation of the FET and the sensor surface is generally referred to as the extended gate configuration, and serves two advantages compared to a traditional ion-sensitive field-effect transistor (ISFET) layout: (1) it enhances operational reliability of the FET by isolating it from direct contact with the liquid-phase analyte, and (2) permits independent development of the sensor electrode from the FET device itself. Graphene can be used as the channel material for the FET since it can be deposited over large areas and has already been demonstrated for use in potentiometric biosensors. The FET and metal traces on-chip are protected by an SU-8 microfluidic isolation layer 22, which is an epoxy based negative photoresist. The SU-8 microfluidic is patterned with openings located only at the sensor and reference electrode surfaces. A membrane 24 is provided in the opening between the sensor electrode and the fabric to provide moisture wicking properties from the fabric to the sensor electrode. Given the aim of this work to integrate the sensors into a mattress, the top of the chip is fitted with a mattress fabric 20. This material must be carefully chosen to absorb sweat and consequently bring it into contact with the sensor's surface.

Figure 2:
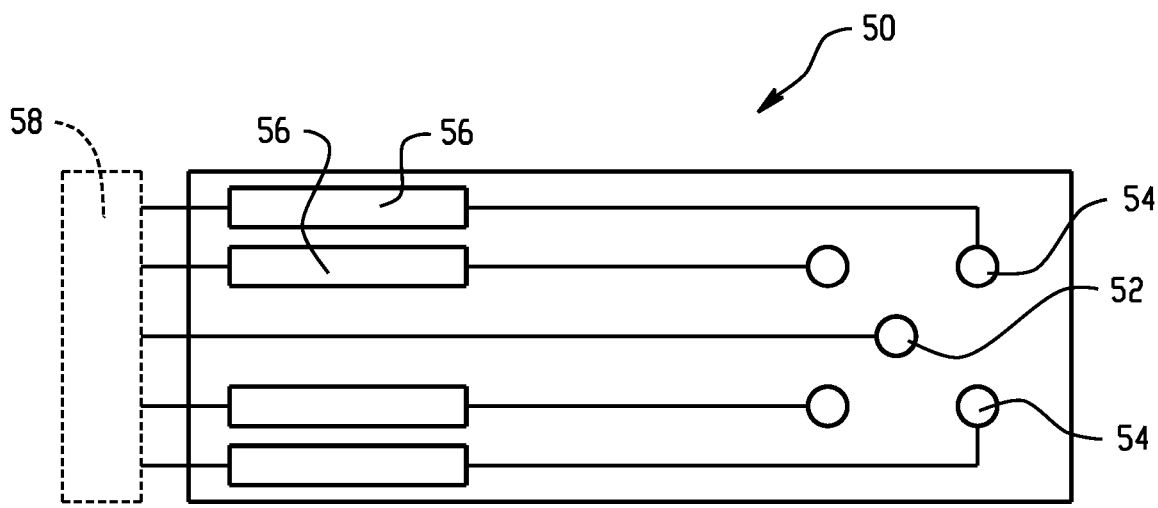
FIG. 2 is a top view of a biosensor array for use in a mattress assembly and/or pillow in accordance with one or more embodiments of the present disclosure.

Referring now to FIG. 2, there is depicted a top down view of an exemplary sensor array 50 that can be implemented using the architecture described above. To minimize size requirements, a common reference electrode 52 is leveraged for multiple, individually-functionalized sensor electrodes 54 to detect different components of sweat. Each of these is connected to a potentiometer 56 (i.e., the high impedance gate of a FET) whose respective signals are fed to a computer or microcontroller 58 that processes the information and makes it available to the user for analysis.

Figure 3:
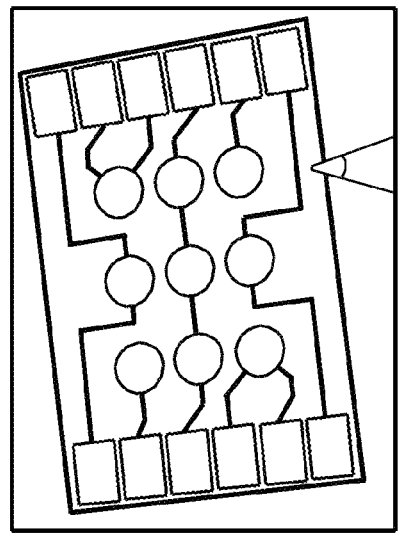
FIG. 3 pictorially depict biosensor arrays in accordance with one or more embodiments of the present disclosure.
Figure 4:
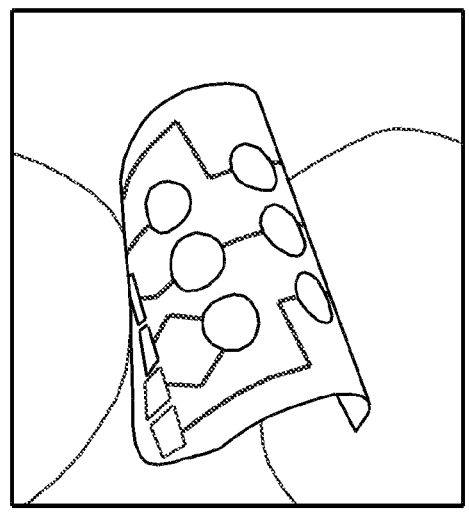
FIG. 4 also pictorially depict biosensor arrays in accordance with one or more embodiments of the present disclosure.
Figure 5:
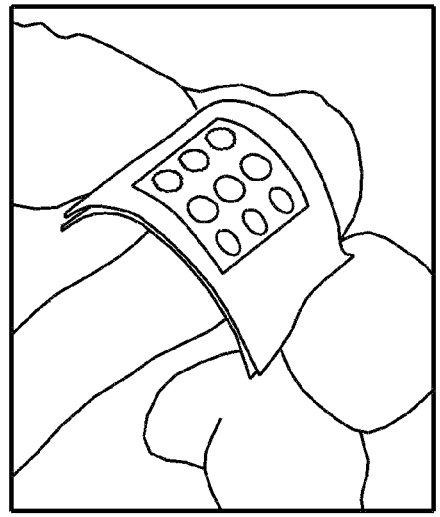
FIG. 5 pictorially depict biosensor arrays in accordance with one or more embodiments of the present disclosure.

FIGS. 3-5 depict various sensors that have been fabricated on both silicon (FIG. 3), polyimide (FIG. 4) substrates, packaged in a substrate (FIG. 5), wherein the various sensors were fabricated using a FET-less fabrication flow, made possible by the extended gate configuration described above. By using flexible substrates, direct embedding of the sensors within a mattress fabric can be achieved, as shown in FIG. 4. In the case where silicon (Si) wafers were used, a thermal silicon oxide ($SiO_2$) was created prior to metal deposition. To improve metal adhesion as well as robustness to wet processing when working with the polyimide substrates, the substrates were first annealed in vacuum at 200° C. for 8 hours, treated with $O_2$ plasma for 60 sec and then both sides were coated with 150 nm of plasma-enhanced chemical vapor deposited PECVD silicon nitride (SiNx) at 100° C. A first metal layer of chrome/gold/aluminum (Cr/Au/Al) with a thickness 25/300/2 nanometers (nm) was deposited using electron-beam evaporation and patterned using lift-off. The top aluminum surface was descummed using an $O_2$ plasma that also facilitates the adhesion of the consequent atomic layer deposition (ALD) of $Al_2O_3$. The $Al_2O_3$ layer was deposited at 250° C. and 150° C. with a thickness of 15 nm, the effects of which are discussed in greater detail below. In order to gain access to the metal layers, vias are etched into the $Al_2O_3$. This was executed using an aluminum specific etchant (based on phosphoric acid) that was heated to 50° C. for 2.5 minutes. The samples were once again descummed with $O_2$ plasma, prior to the electron-beam evaporation of the reference electrodes, which included deposition of titanium/silver (Ti/Ag) thin films having a thickness of 30/150 nm, respectively, which was also patterned using lift-off. SU8-3005, commercially available from Microchem Corporation, Massachusetts, was then spin-coated and patterned, resulting in a 5 micron (μm) thick microfluidic isolation layer. Finally, the exposed Ag thin film is chloridized to Ag/AgCl by drop coating ferric chloride ($FeCl_3$)-based copper etchant for 1 minute, before thoroughly rinsing with deionized water.

To establish a baseline of performance against which to compare the microfabricated sensors, a set of chips was fabricated using shadow masks and tested using polydimethylsiloxane-based (PDMS-based) microfluidics. Since initial process development was performed on Si substrates without temperature constraints, the $Al_2O_3$ layer was deposited at 250° C. The sensor electrodes were connected to the gate of an FET, while the on-chip Ag/AgCl reference electrodes were biased in order to capture the voltage of the gate sensor ($V_{GS}$) for each pH solution. It is known that a change in the pH on the dielectric surface results in an effective change in the threshold voltage (VTH), which can be extracted from the FET's transfer curve. The maximum sensitivity is known as the Nernstian Limit, which corresponds to 59 mV/pH. To establish statistical significance, each measurement was completed four times.

Figure 6:
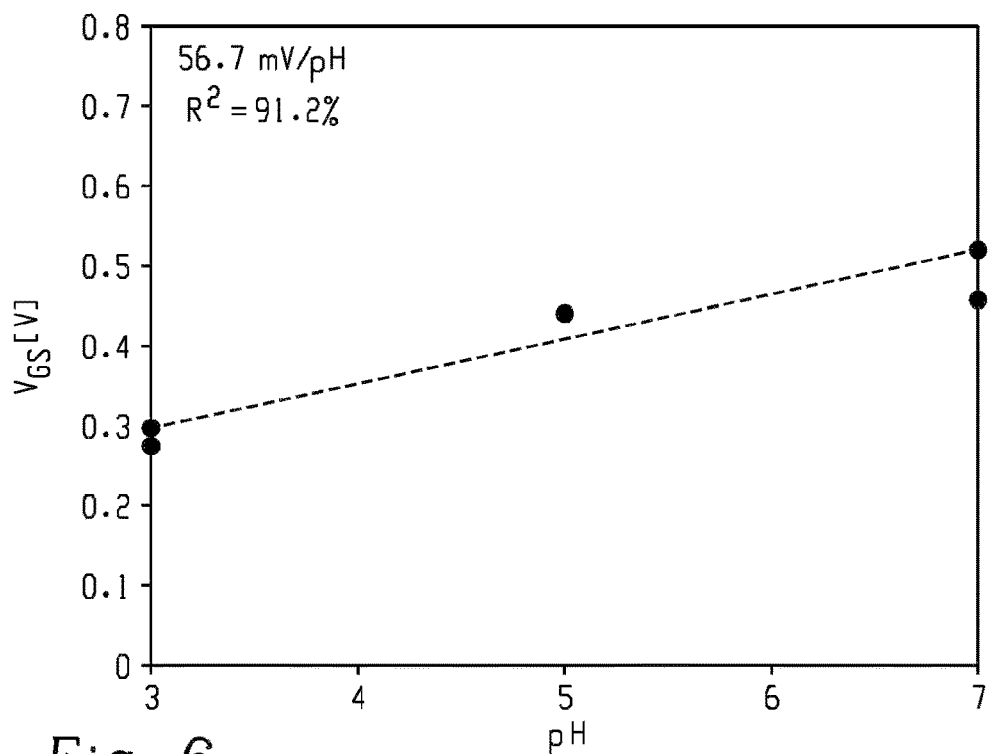
FIG. 6 graphically illustrates $V_{GS}$ as a function of pH for a reference current of 100 nA.

FIG. 6 graphically illustrates the change in $V_{GS}$ for a reference current of 100 nA. From this, it can be gleaned that the sensitivity is 56.7 mV/pH (very close to Nernstian limit) and the linearity is 91.2%.

Figure 7:
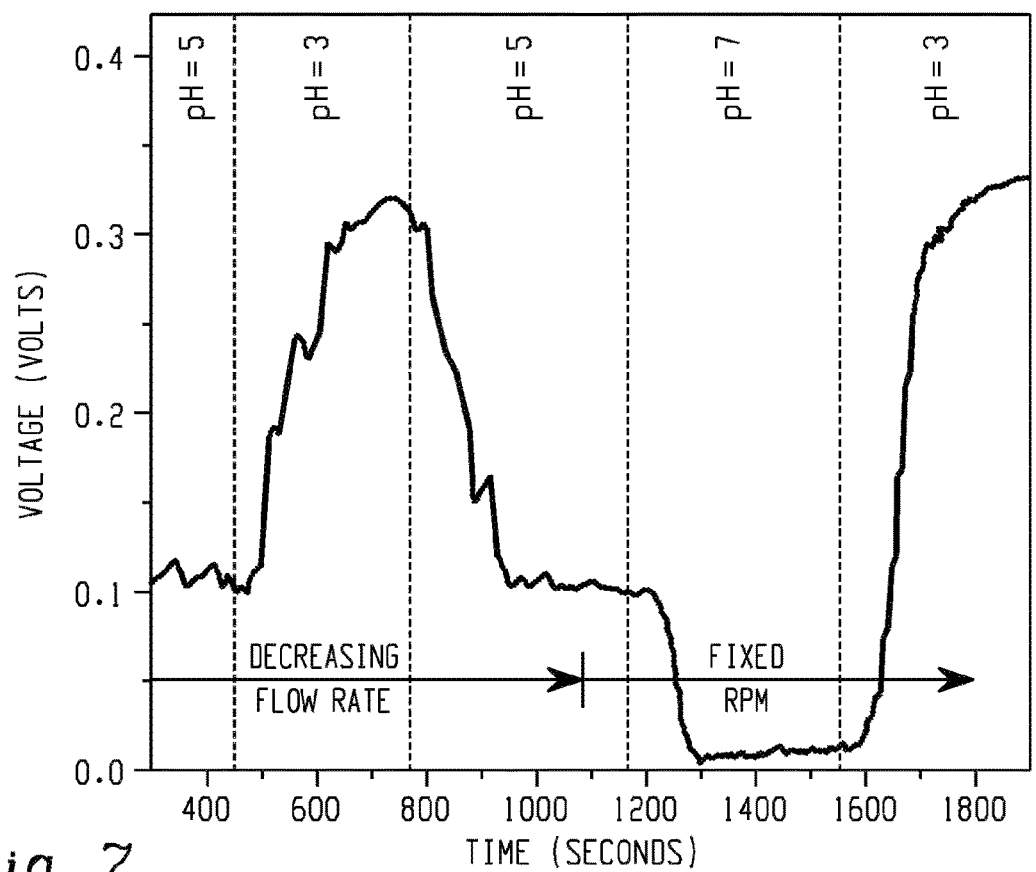
FIG. 7 graphically illustrates a potentiometric transient response of a biosensor array for different pH solutions.

Three samples of mattress material were then evaluated for their suitability of integration with the sensor. This test was conducted by dropping water droplets onto the surface and consequently determining if they were absorbed by the fabric, or retained as droplet. The three materials that were compared were: 1) spun-bonded, nonwoven polypropylene fabric, 2) long staple fiber, needle punched, nonwoven polypropylene fabric, 3) spun bonded and needle punched, nonwoven polypropylene fabric. It was found that only sample 2, the long staple fiber, needle punched, nonwoven polypropylene fabric, absorbed the droplet of water. Samples 1 and 3 exhibited hydrophobic behavior. Given the hydrophilic behavior of sample 2, this particular sample was used to serve as a good top interface for the sweat sensor. To address mattress integration, low-temperature sensor chips were fabricated with a maximum thin film deposition temperature of 150° C. in order to be compatible with the thermal budget of polyimide and other flexible substrates. These chips were first characterized on a silicon-based chip whose backside was attached to soft and flexible PDMS for support while the top was covered with the hydrophilic fabric identified above. Using a peristaltic pump, it was possible to control the flow rate of pH solutions that were dropped onto the fabric to study the effect of flow rate, as well as switch between different pH values to assess sensitivity. Transient data is graphically depicted in FIG. 7. From time (t)=0 to t=1,100 seconds (sec), the flow rate was decreased from 40 RPM to 3 RPM. During this window, there is observable noise in the voltage response. After t=1,100 sec, where the flow rate remains 3 RPM, the noise decreases significantly. The relationship between signal noise and flow rate necessitates further study, and the consideration of design techniques to reduce its effect. Control of the flow rate could be achieved through localized mattress heating and/or iontophoresis. The sensitivity of the response is also non-linear. For the transition between pH=5 and pH=7, the sensitivity was 48.2 millivolts (mV)/pH. This was slightly less than what was observed when high temperature $Al_2O_3$ was used, but still sufficient. Moreover, the sensitivity for the transition between pH=7 and pH=3 increased.

Figure 8:
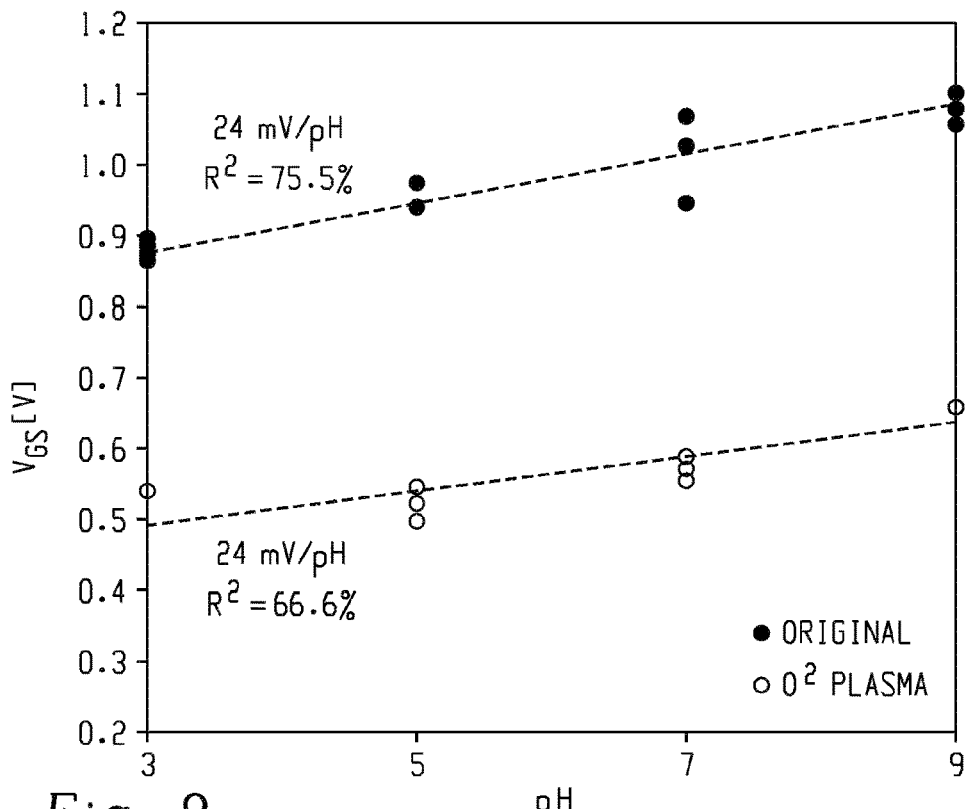
FIG. 8 graphically illustrates $V_{GS}$ as a function of pH for different atomic layer deposition temperatures during formation of the $Al_2O_3$ sensor electrode.

The source of this non-linearity was investigated by examining two variables: (1) the effect of the ALD $Al_2O_3$ temperature, and (2) the on-chip Ag/AgCl reference electrode's stability in liquid. To isolate the impact of ALD temperature on pH sensing performance, sensors with $Al_2O_3$ deposited at 100° C. were tested in PDMS-based microfluidic structures, with current-voltage (I-V) curves extracted from a gate-connected FET and an off-chip flow-through Ag/AgCl reference electrode. As graphically shown in FIG. 8, the sensitivity of these films was found to be 23.8 mV/pH with a significantly decreased linearity of 66.6%. It has been noted in the literature that oxidation of $Al_2O_3$ films can improve pH sensing performance Thus, the sensors were subjected to 30 sec $O_2$ plasma at 50 W before additional testing. The plasma pre-treatment resulted in an improvement in both the sensitivity (34 mV/pH) and the linearity (74.5%). Further investigation is required to understand this effect, though it is hypothesized at this stage that it could be related to the impact of film stoichiometry, with decreased oxygen incorporation in $Al_2O_3$ when deposited at low temperature requiring compensation via $O_2$ plasma versus direct high temperature deposition.

Figure 9:
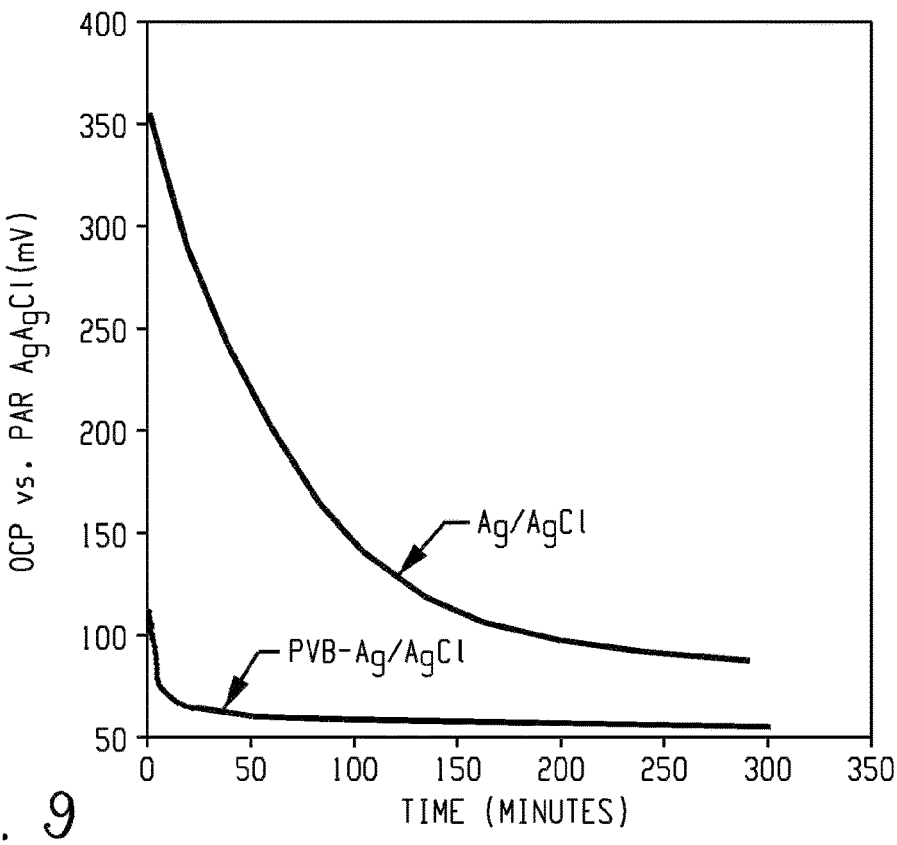
FIG. 9 graphically illustrates drift of an Ag/AgCl reference electrode in potassium chloride over an extended period of time before and after providing a polyvinyl butyral coating thereon.

Most pH sensors in the literature rely on off-the-shelf macroscale Ag/AgCl reference electrodes for demonstration. In benchtop testing scenarios, this is an acceptable approach, however it cannot be adopted in our application, which requires full on-chip integration. It is therefore important to characterize the effect of the thin film-based reference electrode we have constructed. FIG. 9 graphically demonstrates that over a period of 5 hours, a bare Ag/AgCl reference electrode subjected to constant bias in a KCl solution can exhibit over 200 mV of drift. To combat this, previous studies have proposed the use of a polyvinyl butyral (PVB) coating. We have tested this approach and found that it indeed reduces the "burn-in" time required for the electrode to reach a stable state. While other studies have examined these reference electrode preparation techniques for short- to medium-term use (e.g., disposable wearables), further study is required to understand their long-term stability. Care must also be taken to characterize the reference electrode's potential versus pH and ionic strength to ensure stability against these variations.

As noted above, the biosensors described herein can be integrated into the mattress structure. In one or more embodiments, a biosensor array can be layered into the fill of a mattress pad. Typically, a mattress pad has a fill made up of different types of fibers. The biosensors can be integrated into this fiber fill layer, similar to the wiring of a heated blanket. This layer would be directly beneath the end user, so the moisture would not need to travel far to reach one or more of the sensors. All sensors would be connected by wires eventually leading to a cord that can be plugged into a convention outlet. The sensors do need to be powered to work. The sensors would be placed inside the fill in the regions where an end user would typically sweat, e.g., the neck, lower back, and the upper chest.

Figure 10:
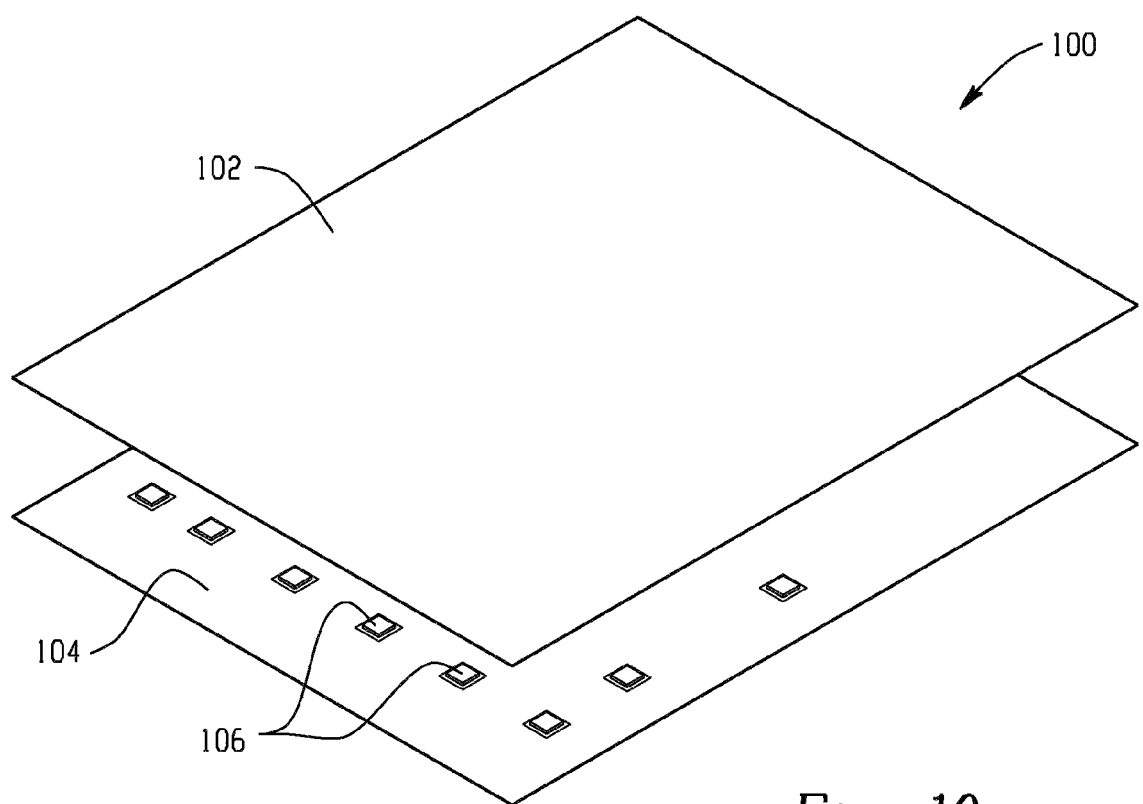
FIG. 10 depicts an exploded perspective view of a mattress pad including a biosensor array in accordance with one or more embodiments of the present disclosure.

FIG. 10 illustrates an exemplary mattress pad 100 including a top panel 102 and a lower panel 104, which are typically stitched about the perimeter. A fiber fill and/or foam fill (not shown) is provided between the panels. The sensor array 106 for analyzing sweat is provided on a selected one of the panels 102, 104.

Figure 11:
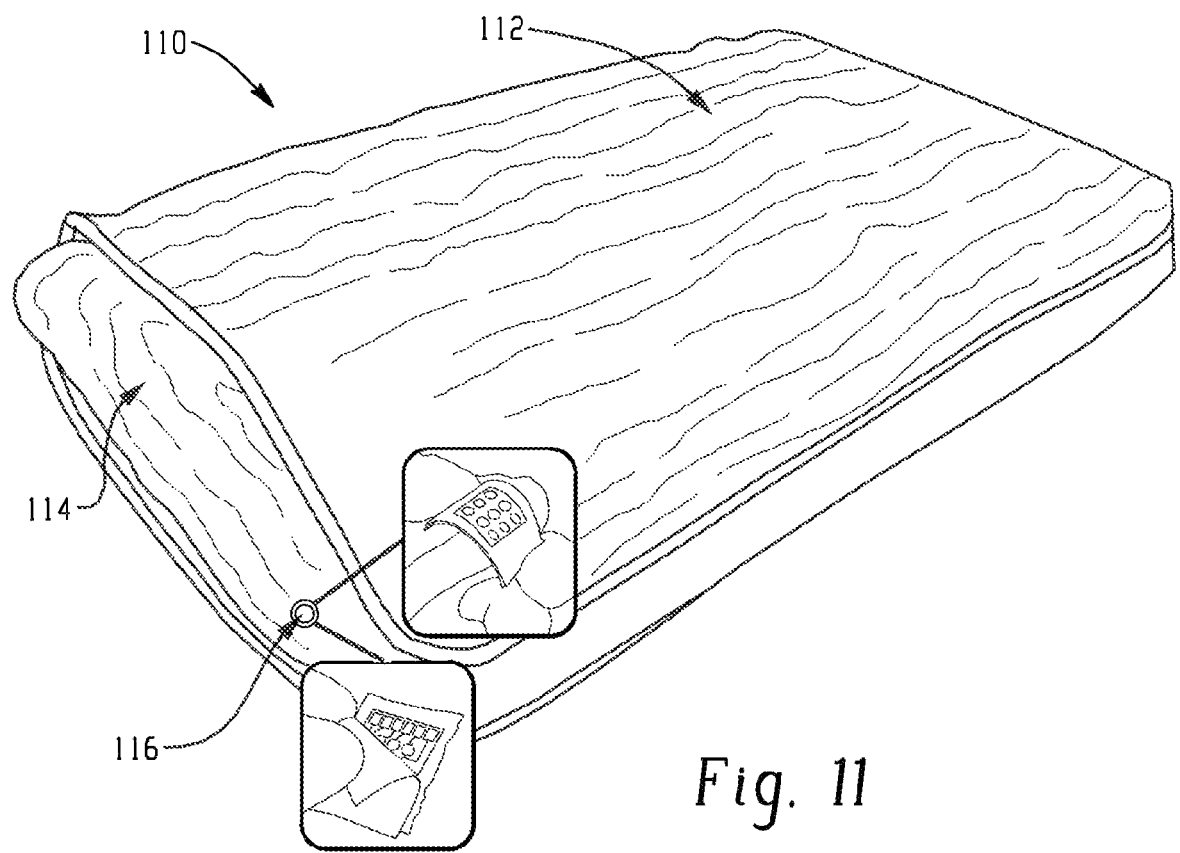
FIG. 11 depicts an exploded perspective view of a pillow including a biosensor array in accordance with one or more embodiments of the present disclosure.

In one or more embodiments, a biosensor array capable of measuring the pH and lactate levels from an end user's sweat can be integrated into a pillow. For example, the biosensor array can be integrated into the scrim of a pillow 110 as shown in FIG. 11. The pillow includes a pillowcase 112, and a pillow cover 114 for enclosing a fill material such as fiber, feathers, foam or combinations thereof, within the pillow covers. The biosensors can be integrated onto the pillow scrim 116, which underlies the pillow cover 114. The biosensor array is secured to the scrim located under a pillow cover (if present) and pillowcase by sewing, glue, or some other means. Sweat travels from the sleeper's head, through the pillowcase and cover to the scrim where its pH level can be measured.

In one or more other embodiments, the biosensors can be integrated onto the pillow cover 114, which underlies the pillow case 112, and in still one or more other embodiments, the biosensors can be integrated onto the pillow case 112.

Figure 12:
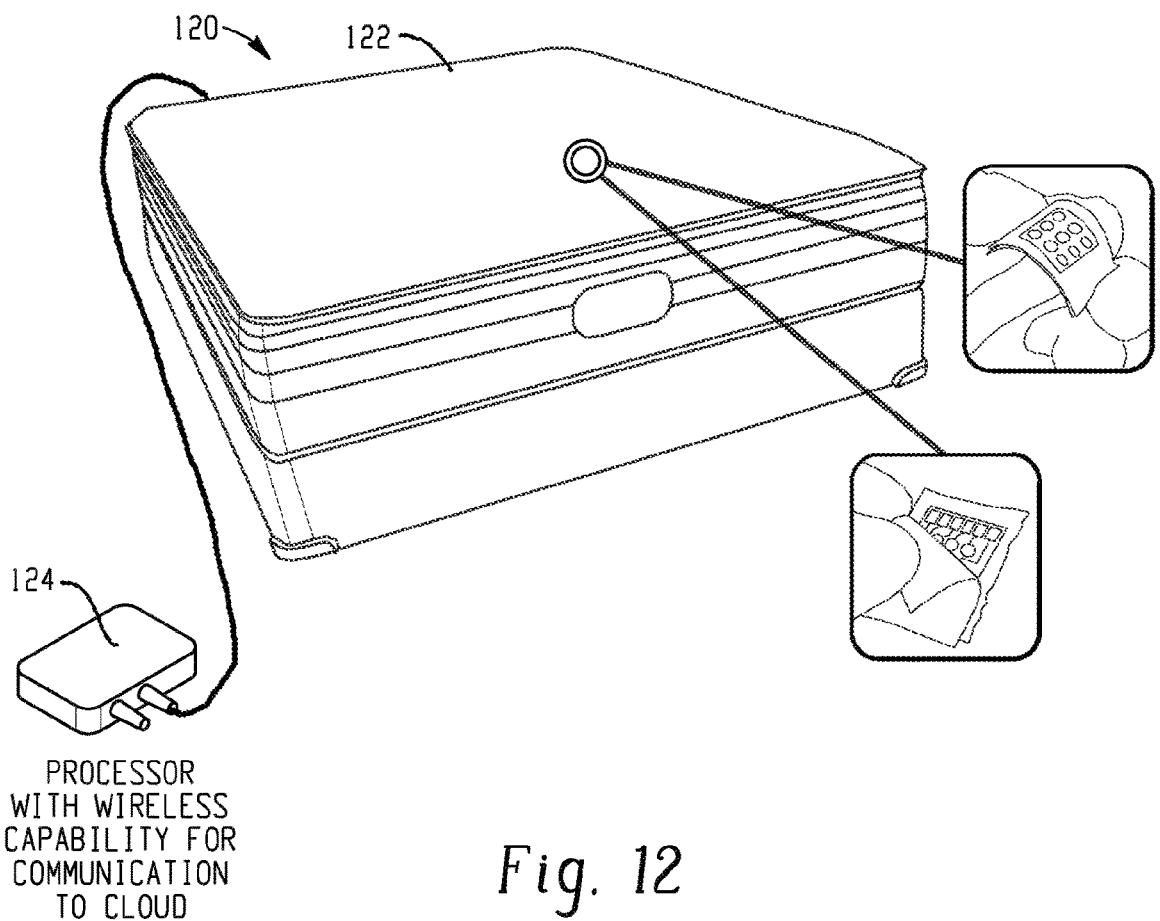
FIG. 12 depicts perspective views a mattress assembly including the biosensor array at various locations in accordance with one or more embodiments of the present disclosure.

In one or more embodiments, the biosensor array can be integrated into a smart mattress 120 as is generally shown in FIG. 12. Integration can be done by printing, gluing, laminating, etc. the sensors into any material, fabric, or foam where moisture and moisture vapor can very easily move through it. The biosensors can be positioned such that the biosensors are located under the neck, lower back, and the upper chest regions of an end user. By way of example, the biosensor array is provided on a top surface 122 of the smart mattress 120. All sensors would be connected by wires eventually leading to a cord that can be plugged in to a conventional outlet. The biosensors array is connected to a processor 124 for analyzing the date received from the sensors. The sensors do need to be powered to work. The biosensors can be part of a larger connected cloud ecosystem where data from the biosensors are streamed via wireless protocols to a secure cloud for data analytics. Eventually this data would be structured and anonymized to share with healthcare providers. In addition, this data would be used in a connected "smart" mattress ecosystem where data from these sensors help would automate the connected smart mattress, its subsystems and additional connected smart home devices. The smart mattress further includes additional sensors such as weight sensors, movement sensors, position sensors, proximity sensors, temperature sensors, pressure sensors, humidity sensors, moisture sensors, gas sensors, optical sensors, combinations thereof, or the like.

Figure 13:
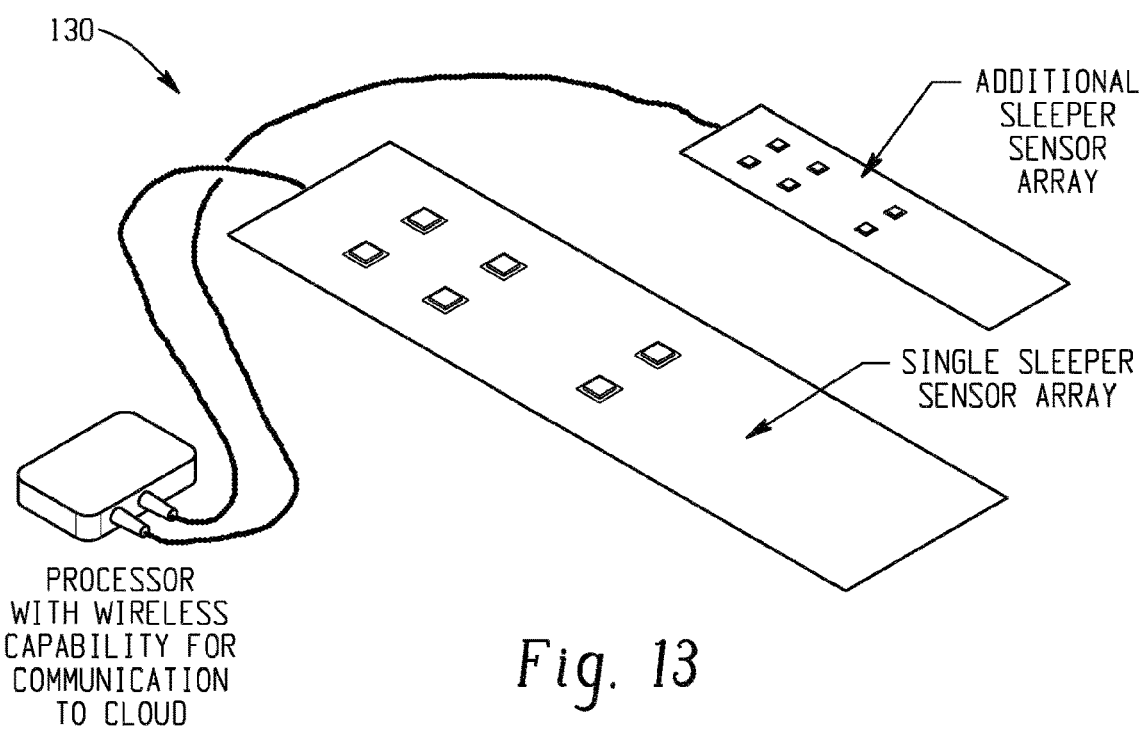
FIG. 13 also depicts perspective views a mattress assembly including the biosensor array at various locations in accordance with one or more embodiments of the present disclosure.

FIG. 13 provides a perspective view of a stand-alone biosensor array 130 that can be positioned/used wherever the end user desires. The standalone sensor array 130 is not integrated into the mattress or any other mattress fabric. Multiple arrays can be connected to a processor, two of which are shown. The stand-alone construction allows the biosensor array 130 to act separate from the mattress and can be placed directly under the sheets of any mattress, for example, and positioned such that the sensors are located under the neck, lower back, and the upper chest. The biosensor array can be built as a single sleeper solution or a dual sleeper solution. In addition, the biosensor array can be deployed in any location of mattress (left, right, center) provided, for mattress applications, that it is directly under the sleeper(s) and the moisture can easily reach one or more sensors in the biosensor array to allow for monitor and analyze sweat. All biosensors would be connected by wires eventually leading to a cord that can be plugged into a conventional outlet. The sensors do need to be powered to work. The sensors can also be part of a larger connected cloud ecosystem where data from the sensors is streamed via a wireless protocols to a secure cloud for data analytics. Eventually this data could be structured and anonymized to share with healthcare providers. In addition, this data could be used in a connected "smart" mattress ecosystem where data from these sensors help would automate the connected smart mattress, its subsystems and additional connected smart home devices.

Figure 14:
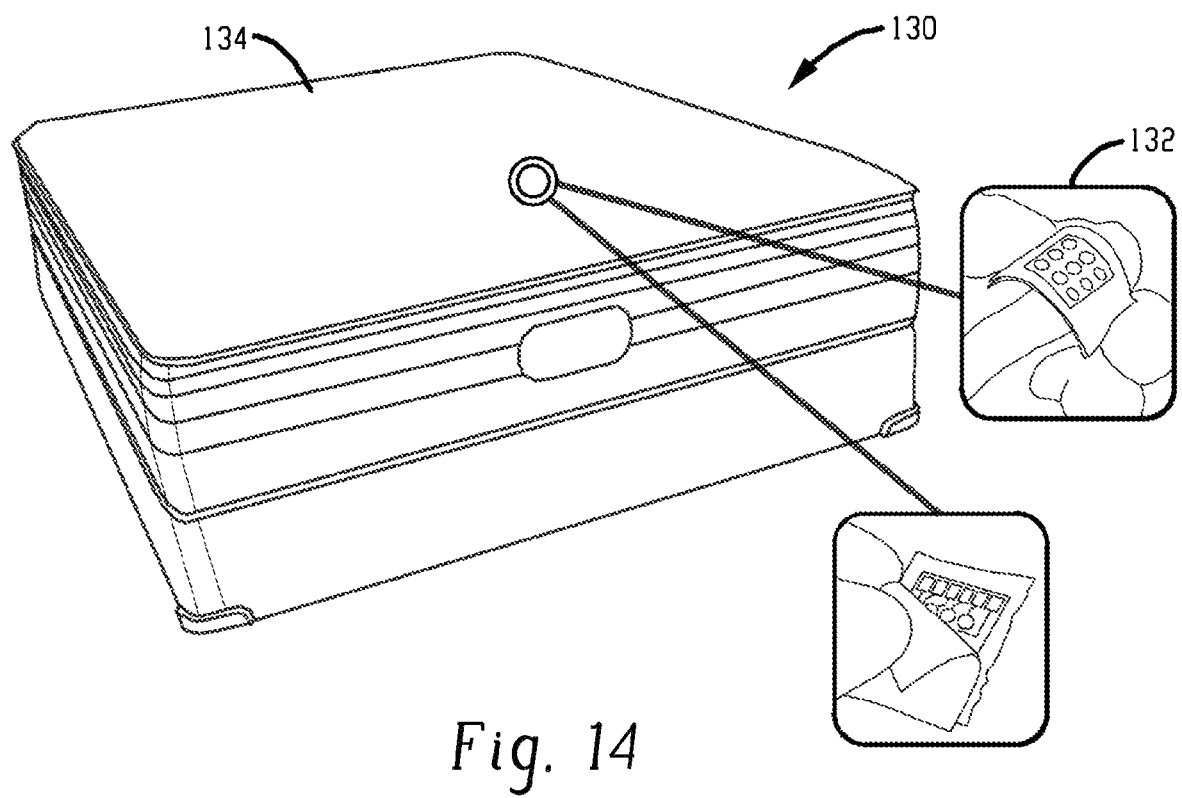
FIG. 14 depicts perspective views a mattress assembly including the biosensor array at various locations in accordance with one or more embodiments of the present disclosure.

FIG. 14 illustrates a perspective view of a mattress 130 including a biosensor array 132 positioned on the knitted fire-retardant material directly underneath the top panel fabric 134. This way the moisture will only need to diffuse through the sleeper's clothing, fitted sheet and the panel fabric before reaching its destination. Any negative impact to the feel of the bed will be reduced, and the sensor will contribute minimal noise when flexed. The sensors will be positioned underneath the torso, head/neck, and/or arm regions of the mattress allowing them to have the best chance to be in contact with the moisture that the sleeper will be giving off.

In one or more other embodiments, the biosensor array 132 can be positioned on an exposed side of the top panel fabric 134. In this embodiment, the moisture will only need to diffuse through the fitted sheet and sleeper's clothing before reaching its destination. The sensor can be aesthetically designed to look consumer-friendly. Any negative impact to the feel of the bed will be reduced, and the sensor will contribute minimal noise when flexed. The sensors will be positioned underneath the torso, head/neck, and/or arm regions of the mattress allowing them to have the best chance to be in contact with the moisture that the sleeper will be giving off.

Figure 15:
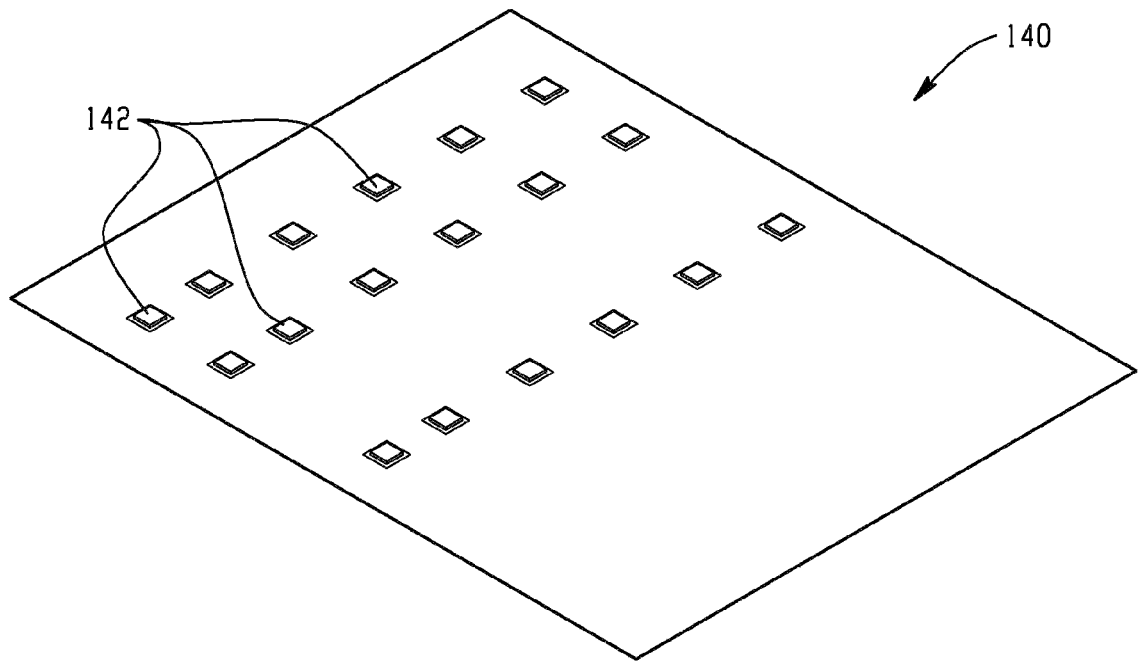
FIG. 15 also depicts perspective views a mattress assembly including the biosensor array at various locations in accordance with one or more embodiments of the present disclosure.

FIG. 15 depicts a three dimensional knitted spacer fabric layer 140 including a biosensor array 142 thereon. The spacer fabric can be used as a layer within a mattress assembly. Spacer fabric is a three dimensional network of small interconnected polymer fibers, which provide an open network. Because of the open structure of this type of material, moisture and moisture vapor can very easily move through it. This makes it an ideal surface for the biosensor to be integrated onto. The moisture can easily reach the sensor and allow for it to work. This spacer fabric layer can go anywhere in the mattress construction including the top layer as some spacer fabrics have an aesthetic component to it. All sensors would be connected by wires eventually leading to a cord that can be plugged in. The sensors do need to be powered to work. The sensors would be placed onto the spacer fabric in the regions where a consumer would sweat; such as the neck, lower back, and the upper chest.

Figure 16:
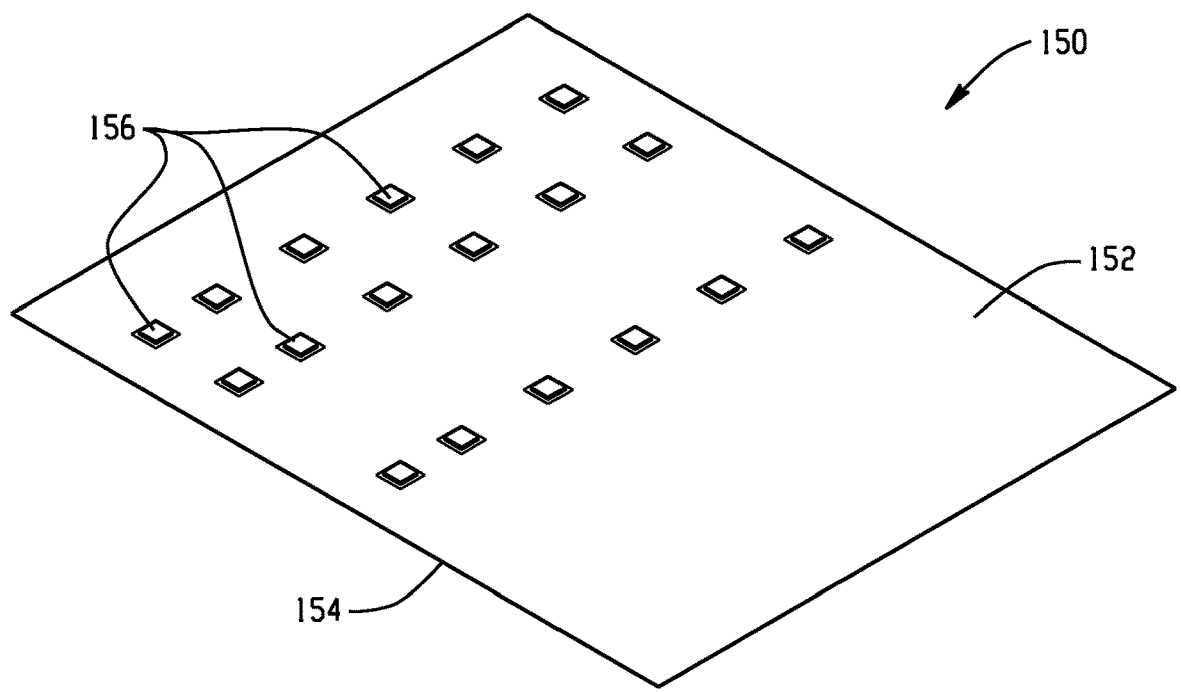
FIG. 16 depicts perspective views a mattress assembly including the biosensor array at various locations in accordance with one or more embodiments of the present disclosure.

FIG. 16 depicts fabric layer 150 including a hydrophilic top surface 152, a hydrophobic bottom surface 154 and, a biosensor array 156 be applied to the top surface 154. The biosensor array 156 can be applied through gluing, laminating, or printing. The hydrophilic side of the fabric will allow moisture to be easily collected due to the water loving nature of this side of the fabric. However, the other side of the fabric is hydrophobic, meaning it does not want to be in contact with water. Therefore, this layer will keep the moisture from moving beyond this layer, allowing for the biosensor to have ample amount of moisture to collect data from. This layer can be placed anywhere in the mattress construction, preferably closer to the sleep surface to increase the amount of moisture applied to the sensor. All sensors would be connected by wires eventually leading to a cord that can be plugged in. The sensors do need to be powered to work. The sensors would be placed on the fabric in the regions where a consumer would sweat; such as the neck, lower back, and the upper chest.

Figure 17:
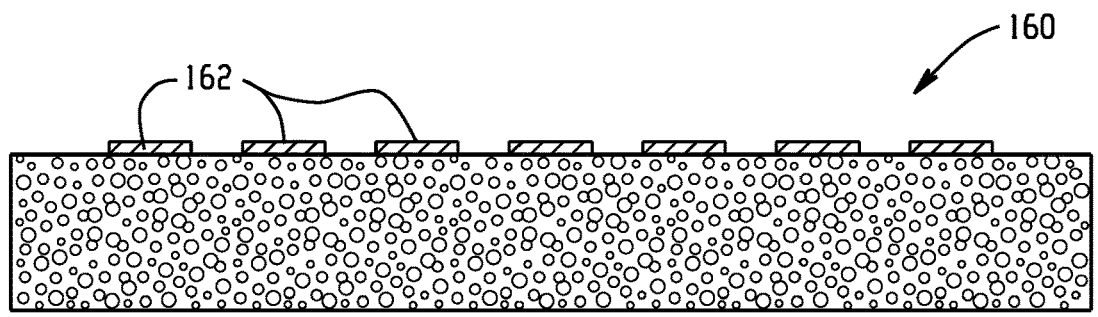
FIG. 17 also depicts perspective views a mattress assembly including the biosensor array at various locations in accordance with one or more embodiments of the present disclosure.

FIG. 17 depicts a polyurethane foam layer 160 for use in a mattress assembly. The polyurethane foam layer includes a biosensor array 162 thereon. In one or more embodiments, the polyurethane foam can be a viscoelastic foam layer. The moisture will need to diffuse through the sleeper's clothing, fitted sheet, panel fabric, and the fire retardant material before reaching its destination. Any negative impact to the feel of the bed will be reduced, and the sensor will contribute minimal noise when flexed. The biosensor array will be positioned underneath the torso, head/neck, and/or arm regions of the mattress allowing them to have the best chance to be in contact with the moisture that the sleeper will be giving off.

Figure 18:
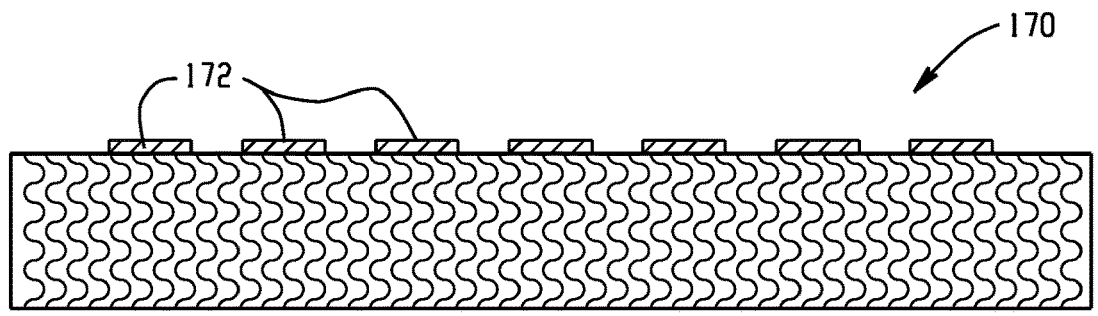
FIG. 18 depicts perspective views a mattress assembly including the biosensor array at various locations in accordance with one or more embodiments of the present disclosure.

FIG. 18 depicts a hydrophilic fabric layer 170 including a biosensor array 172 thereon. The biosensor array can be applied through gluing, laminating, or printing. The hydrophilic fabric will allow moisture to be easily collected and absorbed due to the water loving nature of the fabric. This layer can be placed anywhere in the mattress construction, preferably closer to the sleep surface to increase the amount of moisture applied to the biosensor array. All sensors within the array would be connected by wires eventually leading to a cord that can be plugged into a conventional outlet. The sensors do need to be powered to work. The sensors would be placed on the fabric in the regions where a consumer would sweat; such as the neck, lower back, and the upper chest.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A mattress assembly comprising:
   a flexible biosensor array provided on a layer of the mattress assembly for sensing an electrical conductivity associated with sweat emitted from an end user of the mattress assembly and producing an ionic concentration of at least one analyte, wherein the flexible biosensor array comprises a plurality of sensors, each one of the plurality of sensors comprises a sensing electrode and a reference electrode, wherein the sensing electrode is connected to a gate electrode of a field effect transistor in an extended gate configuration; and
   a processor connected to the flexible biosensor array for interpreting the ionic concentration of the at least one analyte.

2. The mattress assembly of claim 1, wherein the flexible biosensor array is stand-alone and intermediate one or more layers of the mattress assembly.

3. The mattress assembly of claim 1, wherein the flexible biosensor array is in a mattress pad.

4. The mattress assembly of claim 1, wherein the flexible biosensor array is provided on a fire retardant fabric or a fire retardant nonwoven structure.

5. The mattress assembly of claim 1, wherein the flexible biosensor array is provided on a panel fabric on or in the mattress assembly.

6. The mattress assembly of claim 5, wherein the panel fabric is hydrophilic.

7. The mattress assembly of claim 1, wherein the flexible biosensor array is provided on a top panel fabric, wherein the flexible biosensor array and the top panel fabric have an integrated, coordinating aesthetic design.

8. The mattress assembly of claim 1, wherein the flexible biosensor array is integrated with a spacer fabric layer in the mattress assembly.

9. The mattress assembly of claim 1, wherein the flexible biosensor array is provided on a top surface of a fabric, wherein the top surface is hydrophilic and a bottom surface is hydrophobic.

10. The mattress assembly of claim 1, wherein the mattress assembly is a smart mattress comprising additional sensors for measuring weight, movement, position, proximity, temperature, pressure, humidity, moisture, gas and optical properties associated with the end user.

11. The mattress assembly of claim 1, wherein the flexible biosensor array is provided on a surface of a polyurethane foam.

12. The mattress assembly of claim 11, wherein the polyurethane foam is viscoelastic.

13. The mattress assembly of claim 1, wherein the flexible biosensor array is provided in a mattress pad.

14. The mattress assembly of claim 1, wherein the flexible sensor array comprises rigid sensors and a flexible interconnect between the rigid sensors.

15. The mattress assembly of claim 1, further comprising at least one hydrophilic layer, wherein the flexible biosensor array is provided on the hydrophilic layer.

16. A pillow comprising:
    a flexible biosensor array provided within the pillow for sensing an electrical conductivity associated with sweat emitted from an end user of the pillow and producing an ionic concentration of at least one analyte and a processor connected to the flexible biosensor array for interpreting the ionic concentration of the at least one analyte, wherein the flexible biosensor array comprises a plurality of sensors, each one of the plurality of sensors comprises sensing electrode and a reference electrode, wherein the sensing electrode is connected to a gate electrode of a field effect transistor in an extended gate configuration.

17. A mattress pad for a mattress comprising:
    a flexible biosensor array provided on and/or within the mattress pad for sensing an electrical conductivity associated with sweat emitted from an end user of the mattress pad and producing an ionic concentration of at least one analyte and a processor connected to the flexible biosensor array for interpreting the ionic concentration of the at least one analyte wherein the flexible biosensor array comprises a plurality of sensors, each one of the plurality of sensors comprises sensing electrode and a reference electrode, wherein the sensing electrode is connected to a gate electrode of a field effect transistor in an extended gate configuration.

18. A mattress assembly comprising:
    a flexible biosensor array provided on a layer of the mattress assembly for sensing an electrical conductivity associated with sweat emitted from an end user of the mattress assembly and producing an ionic concentration of at least one analyte, wherein the flexible sensor array comprises rigid sensors and a flexible interconnect between the rigid sensors; and
    a processor connected to the flexible biosensor array for interpreting the ionic concentration of the at least one analyte.

* * * * *